United States Patent
Aspelmeyer et al.

(10) Patent No.: US 9,945,996 B2
(45) Date of Patent: Apr. 17, 2018

(54) SUBSTRATE TRANSFERRED MONOCRYSTALLINE BRAGG MIRRORS

(71) Applicant: Crystalline Mirror Solutions GmbH, Vienna (AT)

(72) Inventors: Markus Aspelmeyer, Maria Enzersdorf (AT); Garrett Cole, Vienna (AT)

(73) Assignee: Crystalline Mirror Solutions GmbH, Vienna (AT)

(*) Notice: Subject to any disclaimer, the term of this patent is extended or adjusted under 35 U.S.C. 154(b) by 0 days.

(21) Appl. No.: 13/825,427

(22) PCT Filed: Nov. 8, 2012

(86) PCT No.: PCT/EP2012/072087
§ 371 (c)(1),
(2) Date: Mar. 21, 2013

(87) PCT Pub. No.: WO2013/091986
PCT Pub. Date: Jun. 27, 2013

(65) Prior Publication Data
US 2014/0063606 A1    Mar. 6, 2014

(30) Foreign Application Priority Data
Dec. 22, 2011 (EP) ................................. 11010091

(51) Int. Cl.
*G02B 5/28* (2006.01)
*G02B 5/08* (2006.01)
(Continued)

(52) U.S. Cl.
CPC ............. *G02B 5/288* (2013.01); *G01N 21/31* (2013.01); *G02B 5/0816* (2013.01); *G02B 5/0833* (2013.01); *H01L 33/60* (2013.01)

(58) Field of Classification Search
CPC .... G02B 5/0833; G02B 5/285; G02B 5/0858; G02B 1/115; G02B 5/288; G02B 5/0816;
(Continued)

(56) References Cited

U.S. PATENT DOCUMENTS

2009/0086771 A1   4/2009   Usui et al.

FOREIGN PATENT DOCUMENTS

| JP | 61281203 A | 12/1986 |
| JP | 08330670 A | 12/1996 |

(Continued)

OTHER PUBLICATIONS

Cole et al, Monocrystalline AlxGa1—xAs heterostructures for high-reflectivity high-Q micromechanical resonators in the megahertz regime, Applied Physics Letters, Jul. 2008. pp. 261108-261108-3, vol. 92, No. 26, American Institute of Physics, Melville, NY, USA.
(Continued)

*Primary Examiner* — Jie Lei
(74) *Attorney, Agent, or Firm* — Moore & Van Allen PLLC; Henry B. Ward, III

(57) ABSTRACT

A mirror assembly comprising a carrier substrate; a stack comprising a plurality of alternating monocrystalline semiconductor layers of a first and a second type, wherein the layers of the first type have an index of refraction higher than the layers of the second type thereby forming a Bragg mirror; wherein the carrier substrate is curved having a radius of curvature between 0.1 m and 10 km; wherein the stack is attached to the curved carrier substrate.

18 Claims, 3 Drawing Sheets

(51) Int. Cl.
  *H01L 33/60* (2010.01)
  *G01N 21/31* (2006.01)

(58) Field of Classification Search
  CPC ...... H01S 3/06754; H01S 3/086; H01S 3/082;
       H01S 5/141; H01S 3/109; H01S 3/08059;
       H01L 33/60; G01N 21/31
  USPC ............ 359/337.5, 346, 584, 586, 588, 589;
       372/29.022, 92, 97, 98, 99, 107
  See application file for complete search history.

(56) References Cited

FOREIGN PATENT DOCUMENTS

| | | |
|---|---|---|
| JP | 05346498 A | 12/1997 |
| JP | 2001525999 A | 11/2001 |
| JP | 2009088137 | 4/2009 |
| WO | 9853536 A1 | 11/1998 |

OTHER PUBLICATIONS

Cole et al, Free-standing $Al_xGa1-xAs$ heterostructures by gas-phase etching of germanium, Applied Physics Letters, Jun. 2010, pp. 261102-261102-2, vol. 96, No. 26, American Institute of Physics, Melville, NY, USA.

Yablonovitch et al, Extreme selectivity in the lift-off of epitaxial GaAs films, Applied Physics Letters, Jan. 1987, p. 2222, vol. 51, No. 26, American Institute of Physics, Melville, NY, USA.

Peng et al, Single-crystal silicon/silicon dioxide multilayer heterostructures based on nanomembrane transfer, Applied Physics Letters, May 2007, pp. 183107-1-183107-2, vol. 90, No. 18, American Institute of Physics, Melville, NY, USA.

Rinaldi et al, Advanced Strain Compensation in MBE-Grown Semiconductor Disk Lasers, Mar. 2010, http://www.uni-ulm.de/fileadmin/website_uni_ulm/iui.inst.140/Jahresbericht/2009/ar2009_FR.pdf.

Degallaix et al, Thermal tuning of optical cavities for parametric instability control, Journal of the Optical Society of America, Jun. 2007, pp. 1336-1343.

Kneubühl et al, Laser (Seventh Edition), 2008, pp. 77-81, Vieweg+Teubner, Germany.

| mirror material | absorption coefficient (cm$^{-1}$) | total absorption (ppm) | loss angle (at 300 K) | loss angle (at 4 K) | classification |
|---|---|---|---|---|---|
| AlGaAs DBR (192 nm pen. depth at 1064 nm) | 0,23 | 9 | 3,00E-05 | 5,0E-06 | crystalline |
| SiO$_2$/Ta$_2$O$_5$ DBR (250 nm pen. depth at 1064 nm) | <0,02 | <1 | 4,00E-04 | 3,0E-04 | amorphous |

| substrate material | absorption coefficient (cm$^{-1}$) | total absorption (ppm) | loss angle (at 300 K) | loss angle (at 4 K) | classification |
|---|---|---|---|---|---|
| GaAs wafer (p-type, 6.5x10$^{14}$ cm$^3$, 350 μm thick) | 0,01 | 700 | 1,25E-04 | 1,0E-08 | crystalline |
| GaAs wafer (p-type, 1x10$^{18}$ cm$^3$, 350 μm thick) | 15,4 | 6,6E+05 | 1,25E-04 | 1,0E-08 | crystalline |
| fused silica (SiO$_2$, 12.7 mm thickness) | 2,5E-07 | 0,63 | 5,00E-08 | 5,0E-04 | amorphous |
| Sapphire (single-crystal Al$_2$O$_3$, 12.7 mm thick.) | 5,0E-05 | 127 | 3,00E-07 | 1,0E-08 | crystalline | optical absorption values assume a double pass through the structure (input, then output following reflection)

FIG. 2

SUBSTRATE TRANSFERRED MONOCRYSTALLINE BRAGG MIRRORS

FIELD OF THE INVENTION

The present invention relates to a mirror assembly based on a monocrystalline Bragg mirror bonded to a curved carrier substrate and a process of manufacturing the mirror assembly and an optical resonator system comprising a pair of mirror assemblies forming an optical cavity for application in optical precision measurement systems.

BACKGROUND OF THE INVENTION

Current state-of-the-art multilayer mirrors consist of stacks of dielectric materials, with typical structures using amorphous $SiO_2/Ta_2O_5$ films deposited via ion beam sputtering, IBS. These materials allow for remarkable optical properties showing total absorption less than 1 ppm at a wavelength of 1064 nm. However, recent requirements with respect to the ultimate sensitivity of high performance optical devices such as gravitational wave interferometers and optical reference cavities show that such films exhibit excessively large mechanical dissipation. This dissipation is one of the major factors limiting the overall sensitivity of systems that utilize such high performance optical devices. In depth studies with regard to the coating properties have shown that the mechanical loss of the mirror stack is dominated by the damping in the $Ta_2O_5$ layers. Reduction of this loss has been attempted by modifying this material through doping, annealing, etc. or by replacing the $Ta_2O_5$ with alternative high refractive index films such as Hafnia, $HfO_2$. However, such modifications typically result in less than a factor of two of improvement in the mechanical damping.

SUMMARY OF THE INVENTION

The present invention provides an alternative solution to overcome the above-mentioned problems and to significantly reduce the mechanical damping in the mirror materials.

The invention provides a low absorption crystalline mirror assembly comprising: a carrier substrate; a crystalline stack comprising a plurality of alternating crystalline semiconductor layers of a first and a second type, wherein the layers of the first type have an index of refraction higher than the layers of the second type, thereby forming a Bragg mirror; wherein the carrier substrate is curved having a radius of curvature, ROC, between 0.1 m and 10 m or between 1 km and 10 km; wherein the crystalline stack is attached to the curved carrier substrate.

Within the present application, the term crystalline, single crystal or monocrystalline refers to a low defect density single-crystal film as can be produced via epitaxial growth techniques, such as molecular beam epitaxy, MBE: metalorganic vapor phase epitaxy MOVPE; liquid phase epitaxy, LPE; etc. In this application the terms crystalline and monocrystalline may be used interchangeably. It is important to note that a single crystal or monocrystalline materials structure will still exhibit a finite number of defects or dislocations. However, a monocrystalline material does not contain grain boundaries and defects associated with said boundaries, separating neighbouring crystallites of varying orientation in a polycrystalline sample.

The combination of a curved substrate with a predetermined radius of curvature with the stack of crystalline semiconductor layers provides a highly reflective focusing mirror, which may be used in high performance optical devices. The final carrier substrate may be pre-curved by using a suitable polishing method which provides the surfaces with a predetermined radius of curvature. The stack of crystalline semiconductor layers produces a Bragg mirror at the desired operating wavelength. The combination of a curved substrate and a crystalline stack provides a non-monolithic mirror assembly. This allows for adapting the absorption/transparency properties of the mirror assembly precisely to the needs of the intended application. The choice of ROC depends on the details of the final application and we describe two typical ranges here. For cavities used in high precision spectroscopy, mirrors with ROCs in the range of 0.1 m-10 m are common, though it should be understood that other values are possible. For large scale systems such as gravitational wave detectors, arm-lengths and corresponding ROCs are in the range of 1 km to 10 km. Here again it should be understood that other values for ROCs are possible, with minimum values of 0.1 km or below for small-scale test systems. The term low absorption should be understood to indicate an absorption level with a maximum upper limit of 50-100 ppm. Preferably, this may be reduced to <10 ppm or even into the range below 1 ppm.

For the dielectric multilayer mirrors the thin film stack making up the mirror is referred to as a 'coating'. The term mirror assembly refers to the multilayer stack together with the curved substrate. For our implementation with the bonded crystalline layers, this will be referred to as a transferred mirror assembly. It should be understood that in the latter case the multilayer stack will be crystalline, but the substrate may be a glass, i.e. amorphous or may be crystalline also.

For the semiconductor layers having a higher and a lower index of refraction, respectively, the index of refraction of the "high index" or the "low index" material or both may be varied across the stack. Furthermore, the thickness of layers of a first type and layers of a second type may vary across the stack.

In the mirror assembly the carrier substrate may be transparent, in particular at a wavelength of 1064 nm or 1550 nm, and the surface of the carrier substrate may be polished.

In particular a transparent carrier substrate may have in turn a reduced absorption which may be beneficial for applications with long propagation lengths.

In the mirror assembly the carrier substrate may comprise $SiO_2$, Si, Sapphire, or ultra-low expansion glass, ULE.

Certain choices of materials for the carrier substrate may offer a very similar coefficient of thermal expansion to the transferred stack, e.g. AlGaAs on c-axis oriented Sapphire. Thus, temperature variations may be less likely to introduce stress/strain in the mirror, in particular near the contact surface of the stack with the carrier substrate.

In the mirror assembly the monocrystalline semiconductor layers typically are epitaxial layers based on an AlGaAs ternary alloy, wherein the first and second type comprise $Al_xGa_{1-x}As$ with $0<x<1$; wherein for the layers of the first type x is smaller than for layers of the second type.

In this system a high x yields a lower refractive index, while a low x yields a higher refractive index. Epitaxial AlGaAs with varying Al content thus may provide the possibility for a significant reduction in the mechanical losses, while at the same time providing a high reflectivity and low optical absorption for the mirror.

In the mirror assembly the crystalline stack may be attached to the carrier substrate by at least one of van der Waals forces bonding or covalent bonding.

Using van der Waals bonding, the stacked layers may be attached to the carrier substrate in a process which is easy to realize. The types of bonding, van der Waals bonding and/or covalent bonding may also be combined to a predetermined degree. Also, the bonding step may be combined with or followed by an annealing step. Annealing/heating may be performed at temperatures from just over room temperature up to about 700° C. Temperatures above about 400° C. typically may be applied only when the surface is properly protected, otherwise arsenic may leach out of the AlGaAs.

The invention further provides a method for manufacturing a mirror assembly, comprising a carrier substrate, a stack comprising a plurality of alternating monocrystalline semiconductor layers of a first and a second type, wherein the layers of the first type have an index of refraction higher than the layers of the second type; wherein the carrier substrate is curved having a radius of curvature between 0.1 m and 10 km; the method comprising the steps of providing a first substrate; providing the carrier substrate; epitaxially forming, for example by MBE or MOVPE, the stack of alternating crystalline semiconductor layers of the first and the second type; detaching the stack from the first substrate; attaching the stack to the curved carrier substrate.

The method thus provides a first monocrystalline substrate for forming the stack of layers. After having formed the stack on the first substrate, the stack is lifted off from the first substrate and brought into contact with the surface of the second curved substrate. The stack is thereafter attached to the second substrate forming the transferred mirror assembly. Thereby, a curved monocrystalline mirror stack on a low-optical and mechanical loss substrate may be achieved.

In the method described above, the first substrate may comprise GaAs, or Ge.

The first substrate may in particular be selected based on the operating wavelength for the envisaged application. Thus, various crystalline semiconductor materials systems such as GaAs or Ge may be chosen for the first substrate. Furthermore, InP, or GaN/AlN may also be used.

In the method the carrier substrate may be transparent, in particular at a wavelength of 1064 nm or 1550 nm, and the surface of the carrier substrate may be polished.

In the method, the carrier substrate may comprise $SiO_2$, Si, Sapphire, or ultra-low expansion, ULE, glass.

In the method as described above the crystalline semiconductor layers may be monocrystalline epitaxial layers based on an AlGaAs ternary alloy, wherein the first and second type comprise $Al_xGa_{1-x}As$ with $0<x<1$; wherein for the layers of the first type x is smaller than for layers of the second type.

In the method, the stack may be detached from the first substrate by using chemo-mechanical substrate removal or epitaxial lift-off processes.

The chemo-mechanical substrate removal process may comprise lapping/grinding, wet-etching and other processes.

The stack may be attached to the carrier substrate by at least one of van der Waals forces bonding and covalent bonding.

Bonding may comprise at least one of van der Waals forces bonding or covalent bonding. It may also be possible to use intermediate films such as adhesives or oxides.

The stack may be bonded to the carrier substrate and the bond may be strengthened by annealing.

The annealing step may result in permanent bonding of the stack to the carrier substrate.

The invention also provides an optical resonator for optical precision measurements comprising two mirror assemblies as described above, the reflecting surfaces of the mirrors facing each other at a predetermined distance, wherein for a ROC of 0.1 m to 10 m, a spacer having a predetermined thickness may be interposed between the two mirrors assemblies, wherein the spacer provides the predetermined distance between the two mirrors.

In the optical resonator for optical precision measurements comprising two mirror assemblies as described above, the reflecting surfaces of the mirrors facing each other at a predetermined distance, wherein for a ROC of 1 km to 10 km, each mirror assembly may be individually supported.

The spacer material may have substantially the same optical properties as the mirror substrates. It may also have substantially the same thermal expansion properties as the mirror substrates. Thereby, the spacers will have a minimal influence on the properties of the cavity.

In these applications the use of epitaxial mirror materials for the construction of mirror assemblies as described above allows for a significant increase in the mechanical quality factor of the cavity end mirrors. Thus, the undesired effects of coating-induced phase noise may be minimized and the overall system sensitivity and/or stability may be enhanced. In comparison to other approaches aimed at reducing the deleterious effects of phase noise, e.g. gratings and photonic-crystal reflectors, such transferred epitaxial Bragg mirrors may be employed in existing precision optical systems without necessitating changes in the layout. Replacing the commonly used dielectric stack with a monocrystalline multilayer may offer a reduction in the mechanical damping by a factor of about 10 to a factor of about 100. Thus, significant improvements may be realized with crystalline mirrors. Moreover, such materials may be doped in order to achieve a finite electrical conductivity allowing for charge removal from the surface of the optics.

Previously, epitaxially grown monocrystalline multilayers have not been applied in high performance interferometry or optical reference cavities; this was not pursued because: experts in the field assumed that the absorption would be too high, the mechanical losses had not been measured, and epitaxial films were almost exclusively flat and typically limited to deposition on high absorption semiconductor substrates. In contrast, for the present application for high performance interferometry or optical reference cavities, a curved structure is necessary. However, growing a curved monocrystalline stack via epitaxial deposition methods is extremely difficult, so a transfer and bonding process to remove the flat crystalline multilayer from the 'growth' substrate and bond it to a pre-curved carrier substrate has been developed.

The above and other aspects, features and advantages of the present invention will become more apparent from the following detailed description when taken in conjunction with the accompanying drawings.

BRIEF DESCRIPTION OF THE DRAWINGS

FIG. 2: A table with material properties showing absorption values and mechanical damping for various materials.

DETAILED DESCRIPTION

Figure 1:
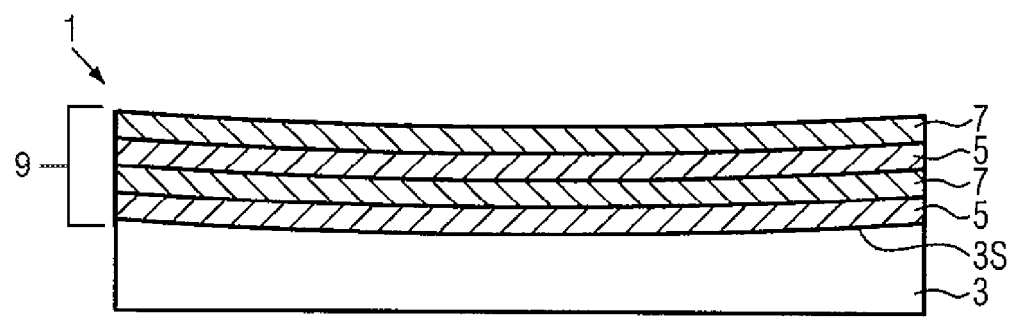
FIG. 1: A side view of a mirror assembly according to the invention.

FIG. 1 shows a side view of a low absorption mirror assembly according to the present invention.

The stack comprises a monocrystalline Bragg mirror bonded to a curved carrier substrate. As described previously, in this application the term monocrystalline refers to a low defect density single-crystal film as can be produced via epitaxial growth techniques, MBE, MOVPE, LPE, etc. In this document crystalline and monocrystalline may be used interchangeably. The mirror assembly 1 of FIG. 1 is only schematically depicted. A curved substrate 3 is provided as the carrier substrate for a stack of monocrystalline layers. The stack 9 of layers 5 and 7 is depicted in a simplification with only four layers, it should be understood, however, that the stack 9 typically comprises many more layers. The maximum reflectivity may be determined by the total number of layers—asymptotically approaching a reflectivity value of 100%. The number of layers for the present example may be about 40 pairs of layers, i.e. 80 total layers, but other numbers of layers such as 100-120 total layers may be used for such a structure. The layers 5 and 7 as shown in FIG. 1 are monocrystalline semiconductors layers alternating with respect to having a high and a low index of refraction, respectively. In FIG. 1, it may be assumed that layers 5 correspond to the layers have a low index of refraction whereas layers 7 correspond to the layers having a high index of refraction. Typically the difference in refractive index should be as large as possible; for example with AlGaAs at a wavelength of about 1064 nm index values of 3.41 and 2.98 may be used for an implementation made from Al(0.12)Ga(0.88)As and Al(0.92)Ga(0.08)As layers respectively.

The stack 9 of FIG. 1 is attached to the carrier substrate 3. The carrier substrate 3 is pre-curved. The curvature may be obtained by using a suitable polishing method that provides the surface with a predetermined curvature. The alternating crystalline semiconductor high- and low-index layers 5 and 7 initially stick adhesively, i.e. via van der Waals forces to the surface of the carrier substrate 3, because the surface 3S of the carrier substrate 3 is polished. Thus, the stack 9 may be put in a predetermined contact position with respect to the curved carrier substrate 3 and may keep that position due to the adhesive force. Typical values of the surface RMS roughness are on the order of 1 nm or below. As indicated above, the layers are formed of alternating $Al_xGa_{1-x}As/Al_yGa_{1-y}As$, $0<x<1$, $0<y<1$ with varying aluminum content. It should be noted that the larger the difference in Al content, the larger the difference in refractive index between the layers. In such a case, it typically takes less layer pairs to reach a high reflectivity. Also the amount of aluminum controls the wavelength at which the layers start absorbing light. A mirror with zero Al content in the high index layers will be transparent to a minimum wavelength of approximately 870 nm at room temperature. Such a mirror may operate with high reflectivity out to a maximum wavelength of about 3 μm with suitable adjustment of the individual layer thicknesses. However, for operation at shorter wavelengths, e.g. for visible light down to 650 nm, the minimum x value corresponding to the Al content may be at least 50%. For a high reflectivity mirror the layer thickness may be a 'quarter wave' in optical thickness wherein the physical thickness, t, for each layer corresponds to the operating wavelength, λ, divided by 4, and divided by the refractive index, n, of the respective layer:

$$t=\lambda/(4*n) \quad (\text{eq. 1}).$$

However, it is important to note that in some implementations the layer thickness may be varied with respect to the thickness t, thus deviating from eq. 1. This may be useful for example for producing so called 'chirped' mirrors, which may have wide operating ranges. Additionally, multi-periodic structures such as "dual-band" or dichroic mirrors may be possible. These structures then may reflect at least two different wavelengths of light. For "chirped" mirrors, the range of wavelengths with high reflectivity may be increased by varying the thickness of the layers, for example by slowly increasing the layer thickness over the vertical direction of the mirror. However, the use of such a varied layer thickness may be at the expense of maximum reflectivity. FIG. 1 shows a high precision optical mirror for which the above equation with respect to the physical thickness holds. Note that by observing eq. 1, the high and low index layers have different thicknesses from each other as their respective refractive index values are different. Furthermore, the carrier substrate may be transparent to reduce absorption effects in large scale applications such as gravitational wave interferometers. These materials may typically include $SiO_2$, Sapphire, Si or ULE. The proper choice of material may also allow for integration of the mirror assembly into optical resonator systems, i.e. using similar or even the same materials as for the spacer that holds the mirrors apart, see also the description of FIG. 3, below.

The radius of curvature, ROC, may typically be between 0.1 m and 10 km. A typical value which is used in applications such as optical reference cavities shown in FIG. 2 is about 1 m. In an extreme case mirrors employed in gravitational wave detectors, for example the Laser Interferometer Gravitational Wave Observatory, LIGO, may have ROCs on the order of 1 km.

FIG. 2 shows a table with a compilation of various materials properties. The optical absorption values assume a double pass of light through the structure, i.e. input of light, then output following reflection at a respective depth into the material, characterized by the optical penetration. The values indicated are the absorption coefficient, the total absorption and the loss angle. The Table of FIG. 2 includes loss angle values at 300 K and at 4 K. Furthermore, the classification of the material as to crystalline or amorphous is indicated. Again, the term crystalline should be understood as monocrystalline whereas the material should exhibit substantially no grain boundaries. The table shows that the use of GaAs as a substrate material for the carrier substrate may be disfavored due to the high absorption value and therefore low optical performance. For the mirror materials, the table of FIG. 2 also shows the improvement in loss angle for AlGaAs by at least an order of magnitude or more in comparison to $SiO_2/Ta_2O_5$.

Figure 3:
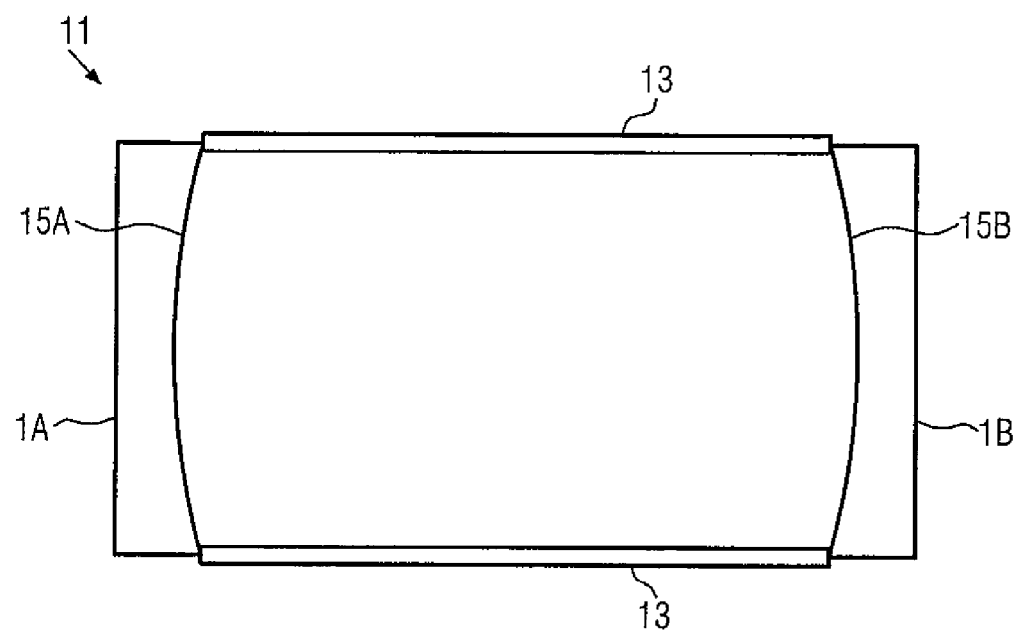
FIG. 3 A cavity with two mirror assemblies according to the invention.

FIG. 3 shows schematically an optical resonator 11 such as a cavity which may be used for high precision optical measurements such as spectroscopy or for stabilization of narrow-linewidth lasers. FIG. 3 shows two Bragg mirrors, 1A and 1B, of the kind as depicted in FIG. 1. The reflecting surfaces 15A and 15 B are facing each other and are separated by a vacuum gap. Interposed between the two mirrors 1A and 1B are spacers 13, which typically are in contact at least with the upper and or lower ends of the mirrors 1A and 1B. The spacers 13 have a predetermined thickness or length so as to provide a fixed distance between the mirrors 1A and 1B.

Additionally or alternatively, there may also be provided at least one support (not shown in FIG. 3) for each mirror so as to fix the position of the mirror and to provide a predetermined distance between the mirrors. In particular, for larger distances between the mirrors, one or more spacers 13 may be difficult to apply such that separate supports may be provided for each mirror assembly. The optical resonator 11 of FIG. 3 may be used for operating wavelengths from about 600 nm to 3 µm, assuming the use of AlGaAs multilayers. It may also be possible to select different ranges of wavelengths by varying the material composition of the monocrystalline mirror layers as well as the layer thicknesses. The optical cavity may be used to produce ultra narrow linewidth, i.e. low noise, laser light. This low-noise laser light may be used to interrogate trapped atoms or ions as in an optical atomic clock, or to generate a frequency comb through a combination with a mode locked laser. Combining such a comb with an additional cavity may be used for the generation of pure microwave tones.

FIGS. 4A-4E depict a sequence of steps in manufacturing the Bragg mirror according to the present invention.

Figure 4:
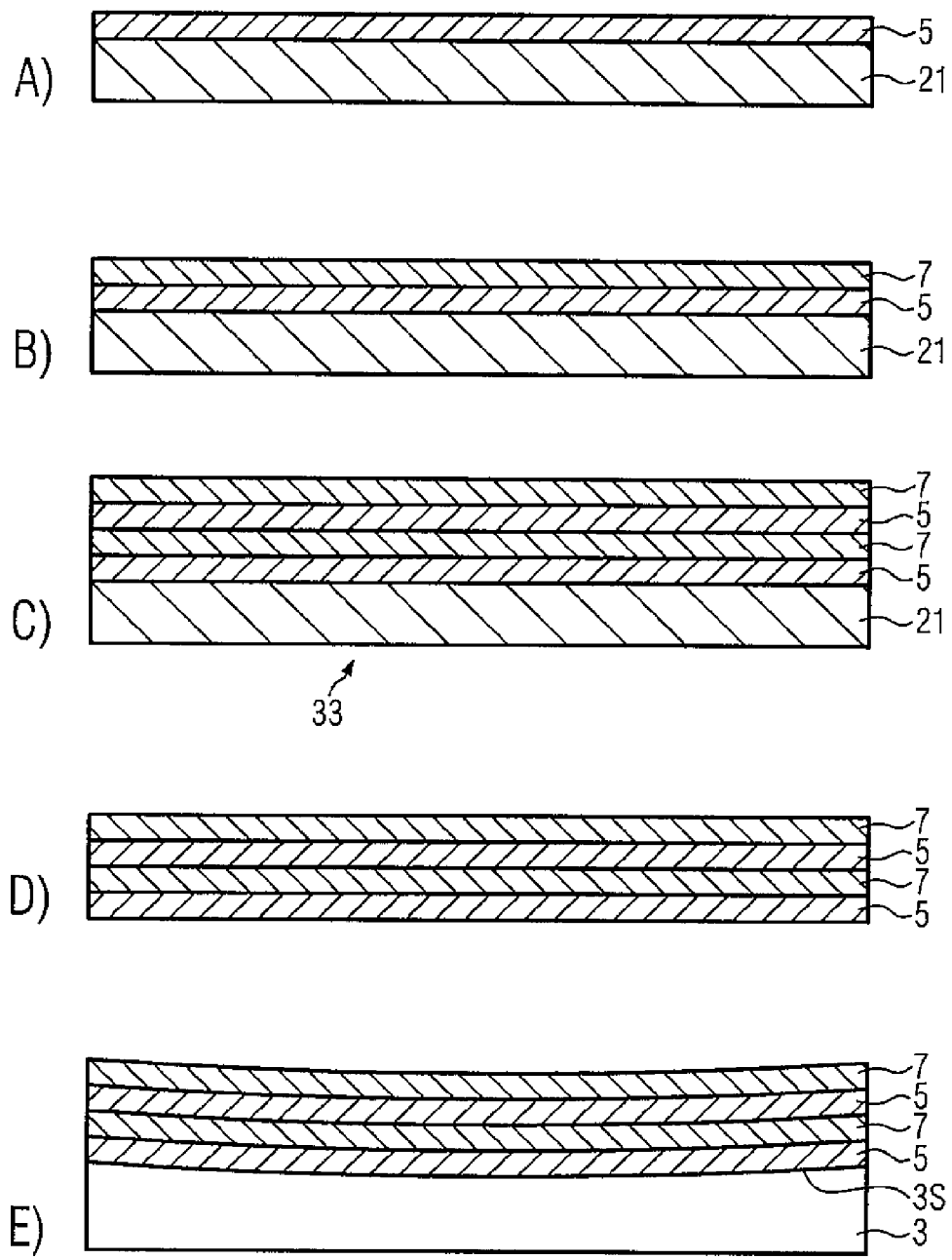
FIG. 4A-4E: Sequence of steps for manufacturing a mirror assembly according to the invention.

FIG. 4A shows a first or donor substrate 21. The first substrate 21 may comprise monocrystalline GaAs or Germanium, although other materials may also be possible, depending on the desired operating wavelength for the application. Such materials may comprise InP, or GaN/AlN. The thickness of the first substrate is typically around 300-500 µm though values between 50 µm and 1 mm are possible. FIG. 4A shows already one layer 5 which is grown on the first substrate 21. This layer 5 as well as further layers may be grown using a suitable semiconductor growth process, such as MBE, and MOVPE.

FIGS. 4B and 4C depict further stages of the manufacturing process. In particular, similar to FIG. 1, only four layers 5, 7, are shown. These layers have alternating refractive indices, as discussed above with respect to FIG. 1. It should be understood that the number of layers may be larger than four.

FIG. 4C also shows that a lift-off process 33 is applied to the combined assembly of first substrate 21 and the layers, 5, 7, forming the stack. It is understood that the stack may substantially be similar to the stack of FIG. 1. The lift-off process 33 may comprise at least one of wet-etching, grinding, lapping, etc. such that the stack is detached from the first substrate 21. Commercially known lift-off processes such as the Smart Cut process involving ion implantation and subsequent annealing may not be applicable to the stack of FIG. 1, due to the overall thickness of the stack and due to the sensitivity of the layers of the stack to disorder, as an ion implantation process may damage the layers. Thus, the lift-off process may comprise the following steps: In a first step, the first substrate 21 is mechanically thinned by, for example, a grinding process. Then, the remaining substrate material of the first substrate is chemically removed, thereby obtaining a detached stack. The detached stack having the first substrate 21 removed is depicted in FIG. 4D.

FIG. 4E shows the stack attached to a second substrate which corresponds to the carrier substrate 3, as shown in FIG. 1. The second substrate 3 may be transparent and polished as discussed with respect to FIG. 1 and in a typical implementation has a pre-determined radius of curvature between 0.1 and 10 m, with a typical value of 1 m or below, or a radius of curvature between 0.5 km and 10 km. The stack is attached to the second substrate 3 by a suitable bonding process, preferably direct bonding through van der Waals interaction, followed by annealing to strengthen the interface and give the possibility of forming covalent bonds. Alternatively or additionally, low temperature bonding with adhesives may be used, or alternative means of adhesion including oxide/oxide bonding, spin-on-glass, etc. may be applicable.

The method as depicted in FIGS. 4A-4E comprises that the mirror layers are initially grown on a flat substrate. That is, both the "donor", also referred to here as the first substrate, and the epitaxial layers are substantially flat. As discussed above, the carrier, or second substrate, has a defined curvature and forces the transferred epitaxial films to then be curved.

The low absorption monocrystalline stack of the mirror assembly typically has a limiting loss angle, i.e. the inverse of the mechanical quality factor, of a maximum of $1 \times 10^{-5}$ to a value below $10^{-6}$. In addition the mirror may typically provide reflectivities>99.99%, with a total absorption at the ppm level at the desired center wavelength. Typical values for center wavelengths are 1064 nm and 1550 nm, though the range of ~600 nm to 3 µm is possible with existing AlGaAs alloys. It should be understood that the loss angle is a materials property that represents an important component of the overall phase noise of the mirror. In present implementations with dielectric mirrors the loss angle of the constituent films is the dominant factor and state-of-the-art precision measurement systems are in many cases limited by Brownian noise of the mirrors, in comparison, the substrate's loss angle can be orders of magnitude smaller with typical materials.

Combining two of these low absorption mirror assemblies as shown in FIG. 3 may provide an optical cavity with a frequency stability corresponding to some parts in $10^{-16}$ to $10^{-17}$ for an averaging time below 1 s. This significantly exceeds current cavity implementations, which typically use conventional dielectric mirrors. The layers described here are monocrystalline, while current implementations employ amorphous dielectric films, i.e. glasses, which are typically deposited via ion beam sputtering directly onto the curved substrate.

The monocrystalline mirror layers typically have a total thickness in the range of 6-10 µm, while the lateral dimensions or diameters vary from about 10 mm up to about 200 mm, and may even exceed 200 mm in extreme applications. As is indicated in the figures, these structures are continuous in the curved plane.

Transparency of the curved carrier substrate is also beneficial for reducing the thermal load in the interferometer/cavity system and to reduce thermo-optic instabilities, particularly for minimizing or even avoiding heating effects that may alter the mirror ROC and cavity length. A typical operating wavelength for the cavity according to the present invention is between 600 nm and 3 µm, with the two most common wavelengths being 1064 and 1550 nm. The thicknesses of the individual layers of the stack are determined by the desired center wavelength, e.g. using the simple quarter wave optical thickness expression given above, with a total monocrystalline layer stack thickness of 6-10 µm. Typical diameters are 10-25 mm, though some applications, e.g. gravitational wave detectors, may require diameters of 200 mm and up.

While the invention has been shown and described with reference to a certain preferred embodiment thereof, it will be understood by those skilled in the art that various changes in form and details may be made therein without departing from the spirit and scope of the invention as defined by the appended claims.

The invention claimed is:
1. A low absorption crystalline mirror assembly comprising:
   a curved carrier substrate; and
   a crystalline stack comprising a plurality of alternating single-crystal semiconductor layers of a first and a second type, wherein the layers of the first type have an index of refraction higher than the layers of the second type, thereby forming a Bragg mirror; wherein the carrier substrate is curved having a radius of curvature (ROC) between 0.1 m and 10 m or between 1 km and 10 km, wherein the crystalline stack being attached to the curved carrier substrate, wherein the crystalline stack is configured to have a limiting loss angle of between $10^{-5}$ and $10^{-6}$ and the crystalline stack is adapted to have a low thermo-mechanical and/or Brownian noise and the crystalline stack has a total thickness of 6-10 µm,
   wherein the single-crystal semiconductor layers of the mirror comprise monocrystalline epitaxial layers based on an AlGaAs ternary alloy, wherein the semiconductor layer of the first and second type comprise alternating $Al_xGa_{1-x}As/Al_yGa_{1-y}As$, $0<x<1$, $0<y<1$, with $x<0.5$ and $y>0.5$.

2. The mirror assembly according to claim 1, wherein the carrier substrate is transparent, in particular at a wavelength of 1064 nm or 1550 nm, and wherein the surface of the carrier substrate is polished.

3. The mirror assembly according to claim 1, wherein the carrier substrate comprises $SiO_2$, Si, Sapphire, or ultra-low expansion (ULE) glass.

4. The mirror assembly according to claim 1, wherein the crystalline stack is attached to the carrier substrate by at least one of van der Waals forces bonding or covalent bonding.

5. An optical resonator for optical precision measurements comprising two mirror assemblies according to claim 1, the reflecting surfaces of the mirrors facing each other at a predetermined distance, wherein for a ROC of 0.1 m to 10 m, a spacer having a predetermined thickness is interposed between the two mirrors assemblies, wherein the spacer provides the predetermined distance between the two mirrors.

6. An optical resonator for optical precision measurements comprising two mirror assemblies according to claim 1, the reflecting surfaces of the mirrors facing each other at a predetermined distance, wherein for a ROC of 1 km to 10 km, each mirror assembly is individually supported.

7. The mirror assembly according to claim 1 having a reflexivity of larger than 99.99% at a center wavelength of between 600 nm-3 µm.

8. A method for manufacturing a low absorption crystalline mirror assembly, the mirror assembly comprising a curved carrier substrate, and a crystalline stack comprising a plurality of alternating single-crystal semiconductor layers of a first type and a second type, wherein the layers of the first type have an index of refraction higher than an index of refraction of the layers of the second type; wherein the carrier substrate is curved, having a radius of curvature (ROC) between 0.1 m and 10 m or between 1 km and 10 km; the method comprising the steps of:
   providing a first substrate;
   providing the curved carrier substrate;
   epitaxially forming on the first substrate the crystalline stack of alternating single-crystal semiconductor layers of the first type and the second type, thereby forming a Bragg mirror;
   detaching the stack from the first substrate; and
   after detaching the stack from the first substrate, attaching the stack to the curved carrier substrate,
   wherein the crystalline stack is configured to have a limiting loss angle of between $10^{-5}$ and $10^{-6}$ and the crystalline stack is adapted to have a low thermo-mechanical and/or Brownian noise, and
   wherein the single-crystal semiconductor layers of the mirror are monocrystalline epitaxial layers based on an AlGaAs ternary alloy, wherein the semiconductor layer of the first and second type are formed of alternating $Al_xGa_{1-x}As/Al_yGa_{1-y}As$, $0<x<1$, $0<y<1$, with $x<0.5$ and $y>0.5$.

9. The method according to claim 8, wherein the first substrate comprises GaAs or Ge.

10. The method according to claim 8, wherein the carrier substrate is transparent, in particular at a wavelength of 1064 nm or 1550 nm, and wherein the surface of the carrier substrate is polished.

11. The method according to claim 8, wherein the carrier substrate comprises $SiO_2$, Si, Sapphire, or ultra-low expansion (ULE) glass.

12. The method according to claim 8, wherein the crystalline stack is detached from the first substrate by using chemo-mechanical substrate removal or epitaxial lift-off processes.

13. The method according to claim 8; wherein the stack is attached to the carrier substrate by at least one of van der Waals forces bonding and covalent bonding.

14. The method according to claim 13, wherein the stack is bonded to the carrier substrate and wherein the bond is strengthened by annealing.

15. The method according to claim 8, wherein epitaxially forming the crystalline stack of alternating single-crystal semiconductor layers of the first type and the second type includes performing molecular beam epitaxy (MBE).

16. The method according to claim 8, wherein epitaxially forming the crystalline stack of alternating single-crystal semiconductor layers of the first type and the second type includes performing metalorganic vapor phase epitaxy (MOVPE).

17. The method according to claim 8 wherein the mirror assembly has a reflectivity of larger than 99.99% at a center wavelength of between 600 nm-3 µm.

18. A low absorption crystalline mirror assembly manufactured according to the method of claim 8.

* * * * *